(12) United States Patent
Johnson et al.

(10) Patent No.: US 7,169,276 B2
(45) Date of Patent: Jan. 30, 2007

(54) CAPILLARY ELECTROPHORESIS METHOD AND APPARATUS FOR REDUCING PEAK BROADENING ASSOCIATED WITH THE ESTABLISHMENT OF AN ELECTRIC FIELD

(75) Inventors: Ben F. Johnson, Palo Alto, CA (US); Eric S. Nordman, Palo Alto, CA (US)

(73) Assignee: Applera Corporation, Foster City, CA (US)

( * ) Notice: Subject to any disclaimer, the term of this patent is extended or adjusted under 35 U.S.C. 154(b) by 486 days.

(21) Appl. No.: 10/075,404

(22) Filed: Feb. 13, 2002

(65) Prior Publication Data

US 2002/0100689 A1     Aug. 1, 2002

Related U.S. Application Data

(63) Continuation of application No. 09/361,485, filed on Jul. 26, 1999, now Pat. No. 6,372,106.

(51) Int. Cl.
G01N 27/447     (2006.01)

(52) U.S. Cl. .................................. 204/451; 204/455

(58) Field of Classification Search ............... 204/451, 204/457, 458, 454, 601, 608, 609, 455
See application file for complete search history.

(56) References Cited

U.S. PATENT DOCUMENTS

| | | | |
|---|---|---|---|
| 5,164,055 A * | 11/1992 | Dubrow | 204/455 |
| 5,221,448 A | 6/1993 | Weinberger et al. | |
| 5,296,116 A | 3/1994 | Guttman | |
| 5,385,654 A | 1/1995 | Kelly et al. | |
| 5,409,586 A | 4/1995 | Kamahori et al. | |
| 5,512,158 A | 4/1996 | Cole | |
| 5,658,446 A | 8/1997 | Yin et al. | |
| 5,728,282 A | 3/1998 | Bashkin et al. | |
| 5,885,432 A | 3/1999 | Hooper et al. | |
| 5,916,426 A | 6/1999 | Madabhushi et al. | |
| 6,372,106 B1 * | 4/2002 | Johnson et al. | 204/455 |

FOREIGN PATENT DOCUMENTS

EP     0 329 341 A2     8/1989

(Continued)

OTHER PUBLICATIONS

McCormick ("Capillary Zone Electrophoretic Separation of Peptides and Proteins Using Low pH Buffers in Modified Silica Capillaries," Anal. Chem. 1988, 60, 2322-2328) ("McCormick").*
Liu et al. ("Separation of Double- and Single-stranded DNA Restriction Fragments: Capillary Electrophoresis with Polymer Solutions under Alkaline Conditions," Anal. Chem. 1999, 71, 1668-1673).*

(Continued)

Primary Examiner—Alex Noguerola
(74) Attorney, Agent, or Firm—Kilyk & Bowersox, P.L.L.C.

(57) ABSTRACT

Methods for reducing peak broadening associated with the establishment of a run field in a capillary electrophoresis process, and apparatus useful for carrying out such methods, are described. Such methods include defining a maximum ramp rate to be used during an initial electric field ramp, defining a minimum period over which the run field is established, and/or maintaining a temperature of a separation medium to within certain ranges during the initial electric field ramp. In addition, methods for determining a ramp rate effective for reducing peak broadening are disclosed.

18 Claims, 11 Drawing Sheets

FOREIGN PATENT DOCUMENTS

| | | |
|---|---|---|
| EP | 0 382 426 A2 | 8/1990 |
| WO | WO 97/24610 A1 | 7/1997 |
| WO | WO 98/10274 A1 | 3/1998 |
| WO | WO 01/07904 A1 | 7/2000 |

OTHER PUBLICATIONS pages 1-5, 5-1 to 5-3, and 5-59 to 5-65 of the Operating Manual for the BioFocus 3000 capillary electrophoresis system downloaded from www.biorad.com.*

CAPLUS abstract of Isaaq et al. ("The effect of column length, applied voltage, gel type, and concentration on the capillary electrophoresis separation of DNA fragments and polymerase chain reaction products," Electrophoresis (1997), 18(7), 1153-1158).*

Kevin D. Altria, "Chapter 6: Optimization of Precision in Quantitative Analysis" Methods in *Molecular Biology*, vol. 52:61-70 *Capiilary* Electrophoresis (1996).

Huan-Tsung Chang and Edward S. Yeung, "Voltage Programming in Capillary Zone Electrophoresis" *Journal of Chromatography*, 632:149-155 (1993).

Hideko Inoue et al., "Enhanced Separation of DNA Sequencing Products by Capillary Electrophoresis Using a Stepwise Gradient of Electric Field Strength," *Journal of Chromatography A*, 802:179-184(1998).

J.H. Knox and K. A. McCormack, "Volume Expansion and Loss of Sample Due to Initial Self-heating in Capillary Electroseparation (CES) Systems" *Chromatographia*, vol. 38, No. 5/6, pp. 279-282 (1994).

Billy A. Williams and Gyula Vigh, "Effect of the Intial Potental Ramp on the Accuracy of Electrophoretic Mobilities in Capillary Electrophoresis" *Analytical Chemistry*, 67: (17: 3079-3081 (1995).

European Search Report of application No. EP 04 01 3127 dated Nov. 11, 2004.

* cited by examiner

CAPILLARY ELECTROPHORESIS METHOD AND APPARATUS FOR REDUCING PEAK BROADENING ASSOCIATED WITH THE ESTABLISHMENT OF AN ELECTRIC FIELD

CROSS-REFERENCE TO RELATED APPLICATIONS

This application is a continuation of U.S. patent application Ser. No. 09/361,485, filed Jul. 26, 1999 now U.S. Pat. No. 6,372,106, which is incorporated herein by reference.

FIELD OF THE INVENTION

This invention relates to methods and apparatus for performing capillary electrophoresis. More specifically, this invention is directed towards methods and apparatus useful for reducing peak broadening caused during the establishment of a run field used to conduct the capillary electrophoresis process.

BACKGROUND

Electrophoretic separations of biopolymers and small molecules are critically important in modem biology and biotechnology, playing a central role in such techniques as DNA sequencing, protein molecular weight determination, genetic mapping, and the like. A particularly preferred electrophoresis format is capillary electrophoresis (CE), where the electrophoresis is performed in a capillary channel having a small internal diameter, e.g., between 5 and 100 µm. In many applications, capillary electrophoresis results in enhanced separation performance over traditional slab-based formats because the superior ability of the narrow-bore capillary to dissipate Joule heat allows for the use of high electrical fields thereby resulting in fast separations in which the effect of analyte diffusion is reduced. In addition, capillary electrophoresis is well adapted to automation because of the ability to automate the steps of sample loading, analyte detection, and replenishment of the separation medium.

Certain commercially important applications of capillary electrophoresis require exquisite separation efficiency. For example, in DNA sequencing separations, plate counts of 20 million plates per meter may be required. In order to achieve this kind of performance, everything possible must be done to reduce instrumental effects that can lead to peak broadening and therefore lower separation efficiencies, e.g., peak broadening caused by the radial temperature profile within the lumen of the capillary, the sample injection volume, solute-wall interactions, siphoning, finite detection volume, and the like (e.g., *Capillary Electrophoresis Theory and Practice*, Chap. 1, Grossman and Colburn, eds., Academic Press (1992)). In addition, because of the high throughput requirements of large-scale DNA sequencing operations, any measures taken to increase the separation performance of the electrophoretic analysis preferably will not substantially reduce the speed, and therefore the throughput, of the process.

Therefore, any further understanding of the mechanisms underlying peak broadening and techniques for reducing the impact of such mechanisms on the performance of CE separations without sacrificing the speed of analysis would be an important contribution to the field of capillary electrophoresis and related applications.

SUMMARY

The present invention is directed towards the discovery of methods and apparatus useful for increasing the separation performance of capillary electrophoresis separations performed in a fluid separation medium by controlling the rate of increase of the electric field strength and/or the temperature of the separation medium during an initial-electric-field-ramp stage of the capillary electrophoresis process.

In one aspect, the invention comprises a capillary electrophoresis method wherein a run field is established during an initial electric field ramp in a controlled manner according to a pre-defined ramp rate. In a preferred embodiment of this aspect of the invention, the run field is established at a ramp rate no greater than about 5 V/cm-s. In another preferred embodiment of this aspect of the invention, the run field is established over a period of at least about ten seconds. In yet another preferred embodiment of this aspect of the invention, the run field is established at a ramp rate which results in a reduction in the amount of peak broadening associated with the establishment of the run field by at least about 10%. In another preferred embodiment of this aspect of the invention, the run field is established at a ramp rate which results in an increase in a length of read of at least about 20 nucleotides over that achieved when the run field is not established in a controlled manner.

In another aspect, the invention comprises a method for producing a desired reduction in an amount of peak broadening caused during establishment of a run field comprising, for each of a plurality of electrophoretic runs, establishing the run field at each of a plurality of different ramp rates, at least some of which ramp rates are not greater than about 5 V/cm-s; analyzing a degree of peak broadening observed for each run; and selecting a ramp rate which is no greater than that which produced a desired reduction in peak broadening.

In yet another aspect, the present invention comprises a capillary electrophoresis method in which analyte species are separated by differential electrophoretic migration through a fluid separation medium located within a capillary under the influence of a run field, an improvement for reducing the peak broadening associated with the establishment of the run field comprising reducing a temperature of an environment surrounding the capillary during an initial electric field ramp. In one preferred embodiment, the temperature of the environment surrounding the capillary is reduced by an amount sufficient to maintain an average temperature of the separation medium during such initial electric field ramp to within about 0.4° C. of the average temperature of the separation medium prior to initiating the initial electric field ramp. In another preferred embodiment, the temperature of the environment surrounding the capillary is reduced by an amount sufficient to maintain an average temperature of the separation medium during such initial electric field ramp substantially constant with respect to an average temperature of the separation medium prior to initiating the initial electric field ramp to an extent sufficient to result in a displacement of the fluid separation medium at an inlet end of the capillary during the initial electric field ramp of less than about 600 µm. In yet another preferred embodiment, the temperature of the environment surrounding the capillary is reduced by an amount sufficient to maintain an average temperature of the separation medium during such initial electric field ramp substantially constant with respect to an average temperature of the separation medium prior to initiating the initial electric field ramp to an extent sufficient to in crease a length of read by at least about 20 nucleotides.

These and other aspects, embodiments and features of the present invent ion will become better understood with reference to the following description, drawings, and appended claims.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that such embodiments are not intended to limit the invention to those embodiments. On the contrary, the invention is intended to cover alternatives, modifications, and equivalents, which may be included within the scope of invention as delineated by the appended claims.

The invention is based in part on the discovery that a substantial amount of peak broadening is caused when a run field is first established, and that such peak broadening can be greatly reduced by establishing the run field in a controlled manner during an initial electric field ramp, and/or by maintaining the temperature of the separation medium at a constant value during the establishment of the run field.

I. Definitions

Unless stated otherwise, the following terms and phrases as used herein are intended to have the following meanings:

"Separation medium" means a medium typically located within the lumen of a capillary through which an electrophoretic separation is conducted. Exemplary separation media include crosslinked gels, un-crosslinked polymer solutions, or polymer-free solvents, e.g., buffered water. Optionally, separation media may include denaturants such as detergents, e.g., SDS, or organics, e.g., urea or formamide.

"Fluid separation medium" means an electrophoretic separation medium that cannot sustain a shearing stress in the absence of motion, i.e., a medium that flows in response to a shearing stress. Examples of fluid separation medium include but are not limited to liquids and liquid solutions, e.g., buffered aqueous polymer solutions.

"Run field" means an electric field used to conduct an electrophoresis separation. Typical run fields used in capillary electrophoresis range from about 50 V/cm to about 3000 V/cm or greater.

"Initial electric field ramp" means an electric field versus time profile during a period in which a run field is initially established.

"Ramp rate" means a run field, E, divided by a total elapsed time of an initial electric field ramp, T. For example, if a run field is 100 V/cm and an initial field ramp takes ten seconds to reach the run field, than the ramp rate is 10 V/cm-s.

"Capillary" or "capillary tube" means tubes or channels or other structure capable of supporting a volume of separation medium. The geometry of a capillary may vary widely and includes tubes with circular, rectangular or square cross-sections, channels, groved plates, and the like. Capillaries may be fabricated by a wide range of well known technologies, e.g., pulling, etching, photolithography, and the like. An important feature of a capillary for use with the invention is the surface-area-to-volume ratio of the capillary lumen. High values of this ratio permit efficient dissipation of Joule heat produced during electrophoresis. Preferably, ratios in the range of about 0.4 to 0.04 $\mu m^{-1}$ are employed. These ratios correspond to surface-to-volume ratios of tubular capillaries with circular cross-sections having inside diameters in the range of about 10 μm to about 100 μm. Capillaries may be formed as individual elements, or as channels formed in a monolithic substrate (e.g., Pace, U.S. Pat. No. 4,908,112; Soane and Soane, U.S. Pat. No. 5,126,022). Capillaries include an "inlet end" through which sample analytes are introduced into the lumen of the capillary.

II. Description of the Preferred Embodiments

When a run field is established in a CE capillary, the temperature of a separation medium located in a lumen of the capillary will generally increase due to Joule heating (e.g., *Capillary Electrophoresis Theory and Practice*, Chap. 1, Grossman and Colburn, eds., Academic Press, (1992)). Joule heating will result in both an increase in the average temperature of the separation medium, ΔT, and the formation of a parabolic radial temperature profile within the separation medium such that the temperature of the separation medium is higher at the centerline of the lumen and lower at the periphery.

The magnitude of the temperature rise ΔT is a function of a number of parameters including but not limited to the shape, materials and dimensions of the capillary, the thermal conductivity of the separation medium and capillary materials, the efficiency of heat transfer between the capillary and the surrounding environment, the electrical conductivity of the separation medium, and the magnitude of the temperature dependence of the electrical conductivity of the separation medium. The magnitude of $\Delta T$ is generally a nonlinear function of these parameters.

Generally, when a material is heated, because of the more intense thermal vibration of its constituent atoms, the material expands. The extent to which a material expands in response to a temperature increase is characterized in terms of its thermal expansion coefficient, where, as used herein, the term "thermal expansion coefficient" means a proportionality constant relating an increase in a dimension of a material, e.g., length, area or volume, to an original dimension of the material, as the result of an increase in the temperature of the material. For example, to a first approximation, the increase in the length of a material due to thermal expansion, $\Delta L/L$, is proportional to the change in temperature, $\Delta T$, according to the relation $$\Delta L/L = \alpha_L \Delta T$$

where $\alpha_L$ is the linear expansion coefficient of the material. However, closer examination shows that $\alpha_L$ is generally not absolutely constant, but rather increases slightly with temperature. Exemplary values of the linear expansion coefficient of several selected materials are given in Table 1 immediately below.

TABLE 1

Exemplary Thermal Expansion Coefficients

| Material | Linear Thermal Expansion Coefficient $\times 10^{6/\circ}$ C. ($\alpha_L$) |
|---|---|
| Fused Silica | 0.5 |
| Borosilicate Glass* | 3 |
| Polyvinylchloride* | 54 |
| Polyethylene* | 180 |
| DI Water** | 360 |
| POP-6 Polymer** | 580 |

*Perry's Chemical Engineer's Handbook, Sixth Edition, page 9–98, Table 6–43, McGraw Hill, (1984).
**Experimentally measured value.

When a fluid material is subject to thermal expansion in a channel having rigid walls and having at least one open end, a flow will be induced, resulting in a finite displacement of the fluid material. The present inventors have discovered that such expansion-driven flows are, under certain operating conditions, present during an initial electric field ramp portion of a capillary electrophoresis process, and that displacements of the separation medium caused by such flows can negatively impact separation performance. Moreover, the inventors have determined this effect has been found to be particularly pronounced in systems similar to those frequently encountered in the CE art, i.e., systems employing a fluid separation medium, a high electric field, and a long narrow channel formed from a rigid material, e.g., a fused-silica capillary tube having an internal diameter of 50 µm and a length of 50 cm. In particular, to a first approximation, in terms of the extent of displacement of the fluid separation medium during an initial electric field ramp, the present inventors have discovered that the displacement will (1) increase with increasing capillary length, (2) will increase with increasing thermal expansion coefficient of the fluid separation medium, (3) will increase with increasing electrical conductivity of the fluid separation medium, (4) will increase with decreasing heat transfer coefficient between the exterior surface of the capillary and the surroundings, (5) will increase with increasing run field, (6) and will increase with increasing capillary internal diameter.

While the foregoing theoretical discussion has been provided to aide in the understanding and description of the present invention, the discussion should in no way be deemed to limit the scope of the invention to this or any other particular theoretical formulation.

In a first aspect, the present invention comprises methods and apparatus for reducing the amount of peak broadening caused by the uncontrolled establishment of a run field in a CE separation employing a fluid separation medium. More specifically, this aspect of the invention comprises a capillary electrophoresis system in which analyte species, e.g., nucleic acids, are separated by differential electrophoretic migration through a fluid separation medium under the influence of a run field E, wherein the run field is established during an initial electric field ramp in a controlled manner according to a defined electric-field vs. time profile having a characteristic ramp rate.

Exemplary preferred electric field vs. time profiles according to the present invention include but are not limited to discontinuous multi-step profiles, continuous linear profiles, continuous non-linear profiles, or combinations of such discontinuous and continuous profiles. In addition, the elapsed time T of the initial electric field ramp and the value of the run field E may vary as required by a particular application. Preferably, the initial electric field ramp will comprise a field vs. time profile that serves to both reduce peak broadening and to achieve the run field E in as short an elapsed time T as possible consistent with the desired reduction in peak broadening.

Figure 1A:
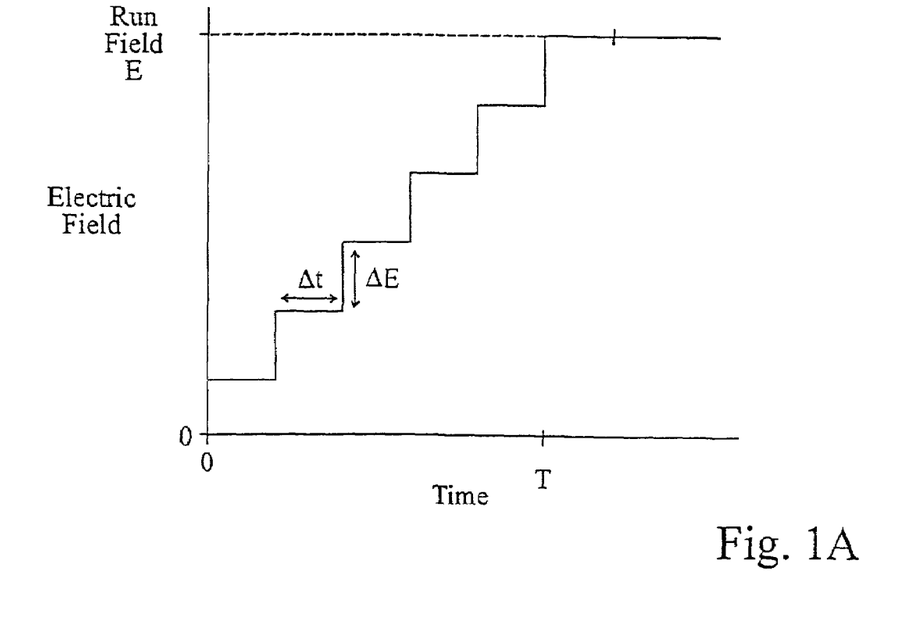
FIGS. 1A, 1B, 1C and 1D show schematic depictions of several exemplary initial electric field ramps comprising various alternative discontinuous multi-step electric field vs. time profiles.

In one preferred embodiment, the initial electric field ramp is characterized by a field vs. time profile comprising a plurality of discontinuous steps where each step is characterized by a particular change in electric field, $\Delta E$, and time, $\Delta t$. FIG. 1A shows a schematic depiction of such a discontinuous multi-step field vs. time profile. Generally, as $\Delta E$ becomes smaller and/or $\Delta t$ becomes larger, the impact of the initial electric field ramp on peak broadening is reduced.

In one particularly preferred embodiment, the initial electric field ramp is characterized by an electric vs. time profile comprising a plurality of discontinuous steps wherein the values of $\Delta E$ and $\Delta t$ for each step are equal, e.g., as schematically depicted in FIG. 1A. Thus, to characterize such an electric field vs. time profile, one need only specify a value for the run field E, the change in electric field at each step $\Delta E$, and the time for each step $\Delta t$.

Figure 1B:
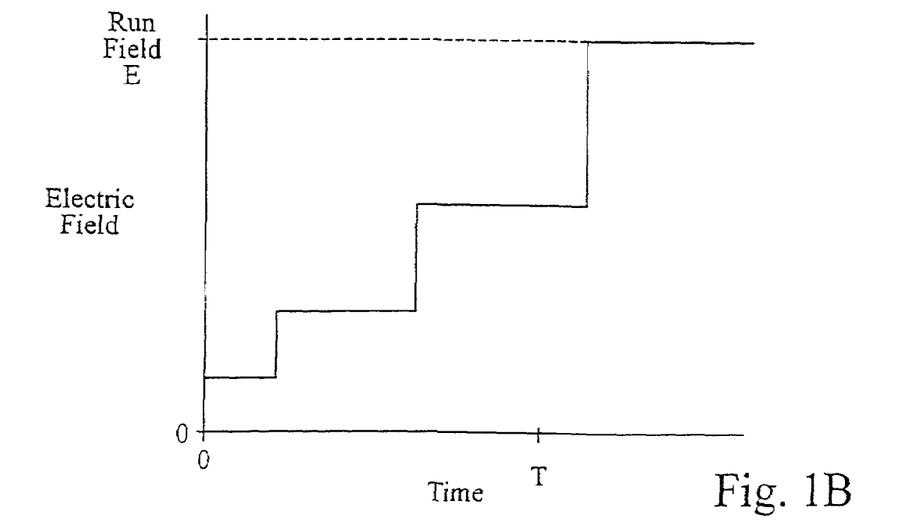
Figure 1C:
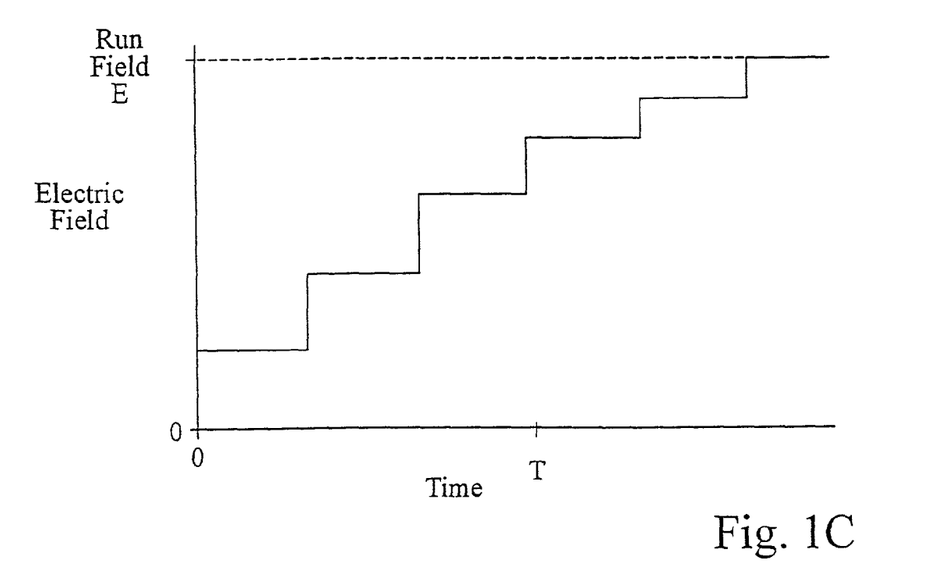
Figure 1D:
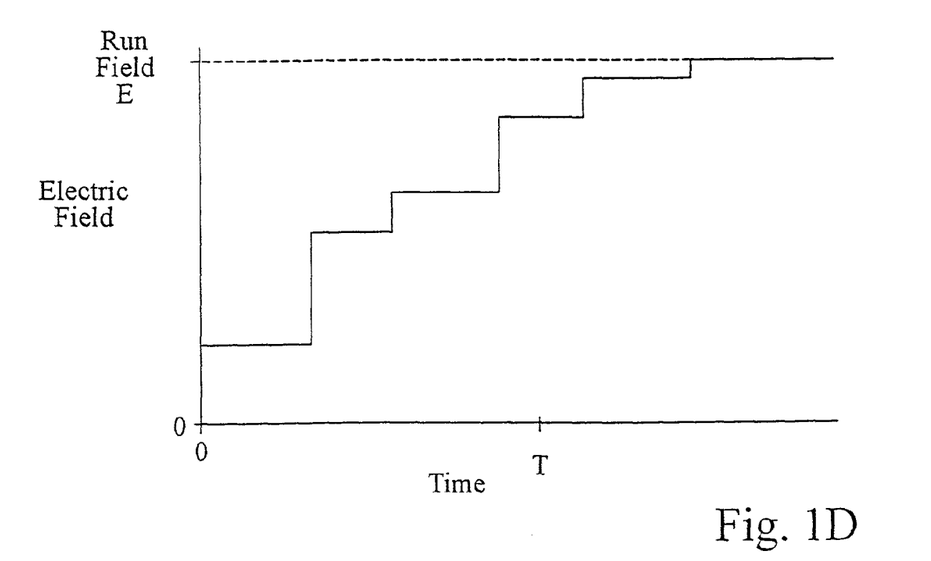

In another preferred embodiment, the initial electric field ramp is characterized by an electric field vs. time profile comprising a plurality of discontinuous steps wherein the values of $\Delta E$ and $\Delta t$ for each step are not equal, e.g., as schematically depicted in FIGS. 1B, 1C and 1D. FIG. 1B shows a schematic depiction of an initial electric field ramp comprising a discontinuous multi-step field vs. time profile in which the values of both $\Delta E$ and $\Delta t$ increase at each step. Alternatively, FIG. 1C shows a schematic depiction of an initial electric field ramp comprising an electric field vs. time profile in which the value of $\Delta E$ decreases at each step and the value of $\Delta T$ is the same for each step. Finally, FIG. 1D shows a schematic depiction of an initial electric field ramp comprising an electric field vs. time profile in which the values of both $\Delta E$ and $\Delta t$ vary chaotically at each step. Because the temperature rise inside the capillary lumen caused by Joule heating is typically an increasing non-linear function of the electrical field strength, the field vs. time profile depicted schematically in FIG. 1C in which the value of ΔE decreases at each step is particularly preferred because it both serves to reduce the impact of the initial field ramp on peak broadening while at the same time reducing the elapsed time T of the initial electric field ramp.

While the values of E, ΔE and Δt will vary depending upon the requirements of a particular application, preferably, when employing an initial electric field ramp comprising a discontinuous multi-step electric field vs. time profile, the value of the run field E is between about 50 V/cm and 3000 V/cm, the time per step Δt is between about 5 s and 200 s, and the change in electric field per step ΔE is between about 1 V/cm and 200 V/cm. More preferably E is between about 80 V/cm and 320 V/cm, Δt is between about 10 s and 100 s, and ΔE is between about 2 V/cm and 60 V/cm.

Figure 2:
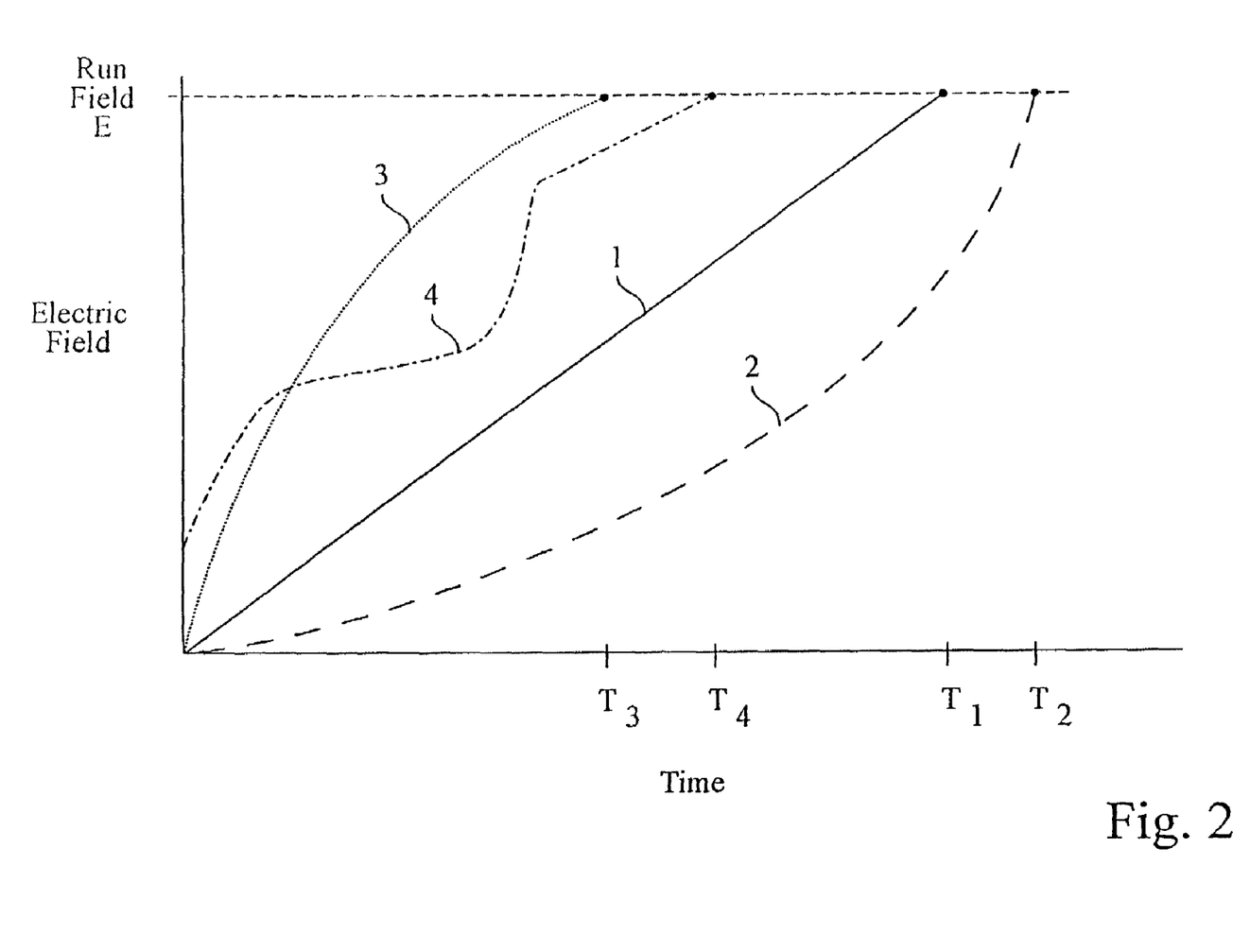
FIG. 2 shows several schematic depictions of exemplary initial electric field ramps comprising various alternative continuous electric field vs. time profiles.

In another preferred embodiment, the initial electric field ramp is characterized by a continuous electric field vs. time profile. As shown in FIG. 2, the continuous electric field vs. time profile may be linear, (e.g., curve 1 in FIG. 2), concave (e.g., curve 2 in FIG. 2), convex (e.g., curve 3 in FIG. 2), or various combinations of linear, concave, and/or convex (e.g., curve 4 in FIG. 2). As discussed with respect to FIG. 1C, preferably the continuous field vs. time profile is linear or convex due to the usual non-linearity of the temperature rise caused by Joule heating.

In another preferred embodiment of this first aspect of the invention, the initial electric field ramp is characterized by a field vs. time profile comprising a combination of a stepped and a continuous profile.

The particular range of values of the ramp rate of the initial electric field ramp that will result in reduced peak broadening and therefore improved separation performance will depend on a number of experimental parameters including the shape, materials and dimensions of the capillary, particularly the length of the capillary, the thermal conductivity of the separation medium and the capillary, the difference in the thermal expansion coefficient of the separation medium and the capillary, the efficiency of heat transfer between the capillary and the surrounding environment, the electrical conductivity of the separation medium, and the temperature dependence of the electrical conductivity of the separation medium. In particular, to a first approximation, a smaller ramp rate will be required with (1) increasing capillary length, (2) increasing thermal expansion coefficient of the fluid separation medium, (3) increasing electrical conductivity of the fluid separation medium, (4) decreasing heat transfer coefficient between the exterior surface of the capillary and the surroundings, (5) increasing run field, and (6) increasing capillary internal diameter.

Therefore, to determine a ramp rate of an initial electric field ramp that will result in reduced peak broadening under a given set of operational conditions, the following procedure may be used. First, for each of a plurality of electrophoretic runs, establish a run field using an initial electric field ramp, where each run uses a different ramp rate, and where at least some of the ramp rates are less than or equal to about five V/cm-s. Next, analyze the extent of peak broadening observed for each run, e.g., by measuring a peak width at half height of a selected peak in each run. Finally, select as the preferred ramp rate one that results in a desired degree of reduction in peak broadening.

Regardless of the particular ramp profile used, e.g., step, continuous, or a combination of stepped and continuous, preferably the ramp rate of the initial electric field ramp is less than about five V/cm-s. More preferably, the ramp rate of the initial electric field ramp ranges from about 0.05 V/cm-s to about 3.0 V/cm-s. In a particularly preferred embodiment, the ramp rate ranges from about 0.1 V/cm-s to about 1.0 V/cm-s.

Alternatively, the run field should be established using an initial electric field ramp having an elapsed time T of at least about ten seconds. More preferably, the run field should be established using an initial electric field ramp having an elapsed time ranging from about 20 seconds to about 500 seconds. More preferably, the run field should be established using an initial electric field ramp having an elapsed time ranging from about 500 seconds to about 4000 seconds.

Preferably, the run field E ranges between about 50 and 3000 V/cm, more preferably between about 80 and 500 V/cm.

In yet another preferred embodiment of this first aspect of the present invention, the run field is established using an initial electric field profile having a ramp rate which results in a reduction in an amount of peak broadening associated with the establishment of the run field of at least about 10% as compared to that found when an initial electric field ramp is not used, and more preferably a reduction in an amount of peak broadening of at least about 25%, and even more preferably a reduction in an amount of peak broadening of at least about 40%.

In another preferred embodiment of the present invention, the analyte species is nucleic acid and the run field is established using an initial electric field profile having a ramp rate which results in an increase in a length of read of at least about 20 nucleotides, preferably about 40 nucleotides, and more preferably about 80 nucleotides, as compared to that found when an initial electric field ramp is not used.

In another aspect, the present invention comprises methods and apparatus for reducing the amount of peak broadening caused by the application of a run field in a CE separation by reducing a temperature of an environment surrounding the capillary during, an initial electric field ramp by an amount sufficient to maintain the average temperature of the separation medium at a substantially constant value during such initial electric field-ramp. As used herein, the term "average temperature" refers to a spatial average temperature where the temperature is averaged across a dimension normal to the direction of electrophoretic migration, e.g., in the case of a cylindrical capillary, the dimension is the radius.

In particular, according to the method of this aspect of the present invention, as the electric field across the capillary is increased during the initial electrical field ramp, the temperature of the environment surrounging the cappillary is reduced by an amount effective to maintain the average temperature of the separation medium located within the lumen of the capillary within about 0.4° C. of the average temperature of the separation medium prior to initiating the initial electric field ramp, more preferably to within about 0.2° C. of the average temperature of the separation medium prior to initiating the initial electric field ramp, and even more preferably to within about 0.1° C. of the average temperature of the separation medium prior to initiating the initial electric field ramp.

In another preferred embodiment of this second aspect of the present invention, during the initial electric field ramp, the temperature of the fluid separation medium located within the lumen of the capillary is maintained constant with respect to the average temperature of the separation medium prior to initiating the initial electric field ramp by reducing the temperature of the environment surrounding the capillary by an amount sufficient to result in a displacement of the fluid separation medium at an inlet end of the capillary during the initial electric field ramp of less than about 600 µm, and preferably less than about 200 µm, and more preferably less than about 20 µm.

In one preferred embodiment of this aspect of the invention, the temperature of the separation medium located within the lumen of the capillary is monitored by measuring the relationship between the electric field applied across the capillary and the measured current passing through the capillary. By knowing how the conductivity of a particular separation medium varies as a function of temperature, it is possible to obtain an accurate measure of the temperature of the separation medium as the electric field is increased. Thus, as the temperature of the separation medium begins to rise, the temperature of the surroundings is lowered using active feedback control. Alternatively, the temperature of the separation medium located within the lumen of the capillary is maintained substantially constant using a pre-programmed temperature ramp based on prior knowledge of the medium's temperature vs. electric field characteristics.

For the most part, with the exception of the improvements embodied in the present invention, the methods and apparatus used to carry out the CE separations according to the present invention may be performed using conventional CE methods and apparatus, as generally described elsewhere (e.g., *Capillary Electrophoresis Theory and Practice*, Grossman and Colburn, eds., Academic Press (1992)). For example, standard capillary tubes, e.g., polyimide-coated fused silica capillary tubes, fluid separation medium, e.g., buffered polymer solutions or polymer free buffer solutions, sample injection techniques, e.g., electrokinetic or hydrodynamic injection, automated system control devices, e.g., a digital computer, and detection techniques, e.g., fluorescence or optical absorbence, may utilized to practice the methods of the invention.

However, CE systems used to carry out the methods of the present invention include certain non-standard features and capabilities. The power supply portion of a CE system for use in the present invention should be controllable by a programmable electronic controller, e.g., a personal computer, so as to allow for the control of an electric field vs. time profile of an initial electric field ramp. In addition, where active feedback control of the initial electric field ramp is used, the electronic controller should be connected to a current monitor for monitoring the electric current passing through the electrophoresis capillary and be able to automatically adjust the electric field across the capillary in response to the current measurement. Also, the CE system for use with the present invention should employ a temperature control system for controlling the temperature of the environment surrounding the capillary channel. The temperature control system should be capable of controlling the temperature of the surrounding environment to within about 0.1° C. along substantially the entire length of the capillary, be capable of changing the temperature of the surrounding environment in increments of 0.1° C., and be capable of adjusting the temperature of the surrounding environment during an initial electric field ramp, where, optionally, such changes are in response to changes in the temperature of the separation medium located in the capillary lumen.

III. EXAMPLES

The invention will be further clarified by a consideration of the following examples, which are intended to be purely exemplary of the invention and not to in any way limit its scope.

Materials and Methods

All electrophoretic separations were performed using an ABI PRISM™ 3700 DNA Analyzer (PE Biosystems, p/n 4308058) equipped with a 50 cm capillary array (p/n 4305787). The 3700 system includes approximately 96 separate fused-silica separation capillaries, each capillary having an uncoated interior surface, a total length of 50 cm, an effective separation length of 50 cm, and in internal diameter of 50 µm. Fluorescence detection of the sample analytes in the 3700 system is accomplished using a sheath-flow detection system (e.g., Kambara et al., U.S. Pat. No. 5,529,679; Dovichi et al., U.S. Pat. No. 5,439,578).

A standard sample mixture comprising 20 single stranded DNA fragments having sizes of 35, 50, 75, 100, 139, 150, 160, 200, 250, 300, 340, 350, 400, 450, 490, 500, 550, 600, 650, and 700 nucleotides was used to characterize separation performance under various operating conditions. Each fragment of the mixture was labeled with TET dye. The sample mixture was dissolved in deionized formamide and 0.3 mM disodium EDTA to a final concentration of about 0.03 nM.

The temperature of the capillary array was maintained at 50° C.±0.1° C. Samples were electrokinetically injected into the capillaries by applying an electric field of 50 V/cm for 30 s while the inlet ends of the capillaries were immersed in the sample mixture.

The separation medium used was a modified version of the commercially available ABI PRISM™ 3700 POP6 polymer (PE Biosystems, p/n 4306733) in which the denaturant was replaced with an alternative denaturant comprising urea at a concentration of either 6M or 8M. The POP6 polymer is a solution of a linear substituted polyacylamide.

Each electropherogram was characterized using a parameter called the "limit of resolution," or "LOR." The LOR is defined as a point in an electropherogrm, expressed in terms of the size of a polynucleotide fragment located at that location in the electropherogram, at which the following relation is satisfied, $$0.5 = \frac{X_2 - X_1}{1/2(W_1 + W_2)}$$

where $X_2$ is the location of the center of a peak 2, $X_1$ is the location of the center of a peak 1, $W_1$ is the peak width at half height of peak 1, and $W_2$ is the peak width at half height of peak 2, where peaks 1 and 2 are DNA fragments that differ in size by a single nucleotide. Because the actual fragments in the standard mixture differ in size by more than a single nucleotide, the single-nucleotide interval $(X_2-X_1)$ was estimated by plotting the position X of each of the 20 fragments in the sample mixture as a function of size, fitting the data points with a third-order polynomial, and determining a single-nucleotide calculated interval $(X_2-X_1)$ based on an interpolation of the resulting fitted curve. The peak widths at half height, $W_1$ and $W_2$, were estimated by assuming that the peak widths for fragments differing in size by a single nucleotide were the same as those of the nearest peaks of the 20 actual peaks. In practice, actual automated base-calling algorithms can typically call bases 100 to 200 nucleotides past the LOR, thus, if for a given separation the LOR was 500, one could expect accurate (i.e., greater than about 98% accuracy) base calling out to about 700 nucleotides.

Example 1

Effect of Run Voltage on the LOR in Two Different Separation Media

Figure 3:
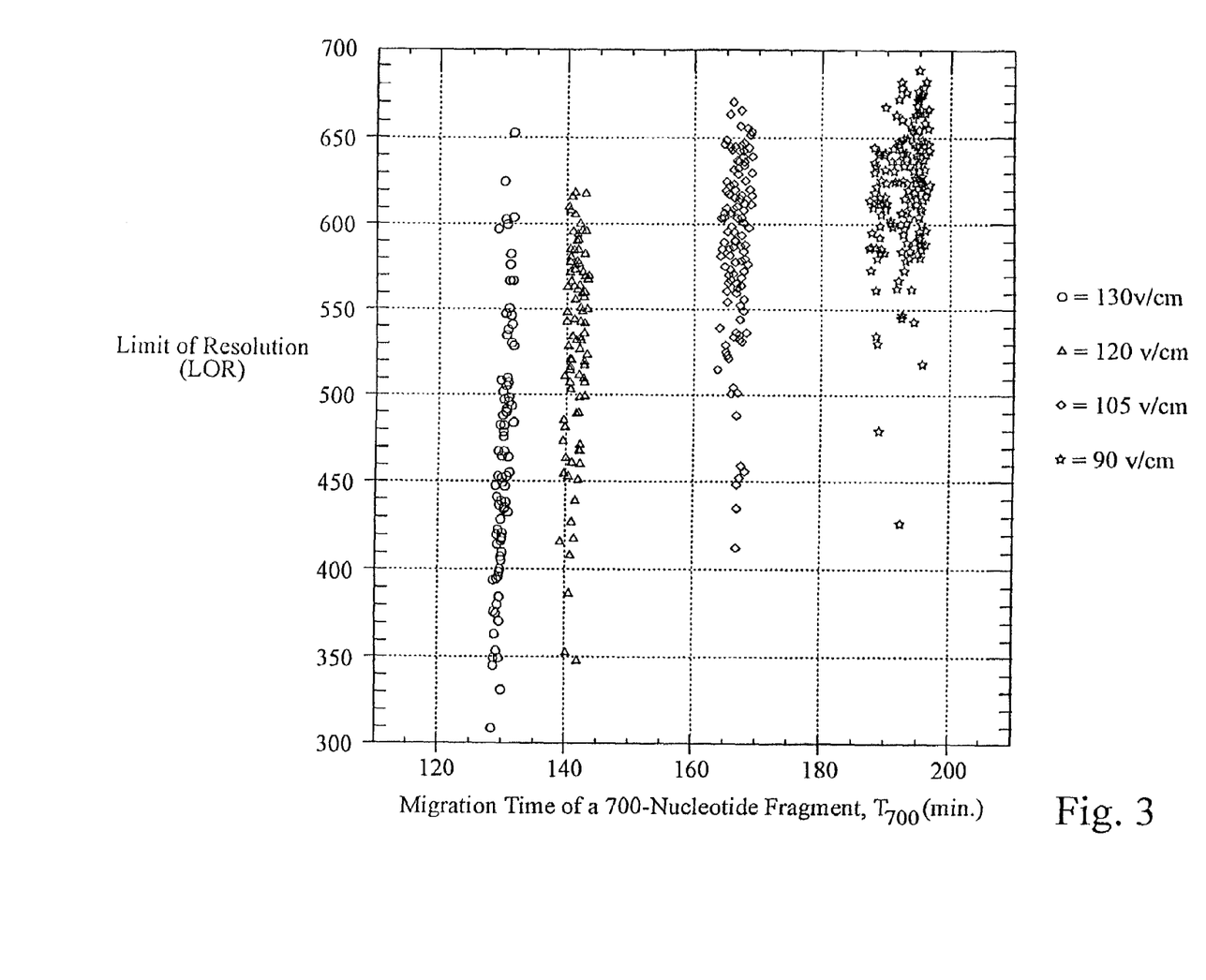
FIG. 3 shows a plot of LOR vs. migration time of a 700-nucleotide DNA fragment in approximately 96 different capillaries at each of a number of run fields without the use of an initial electric field ramp and using a separation medium containing 8M urea.
Figure 4:
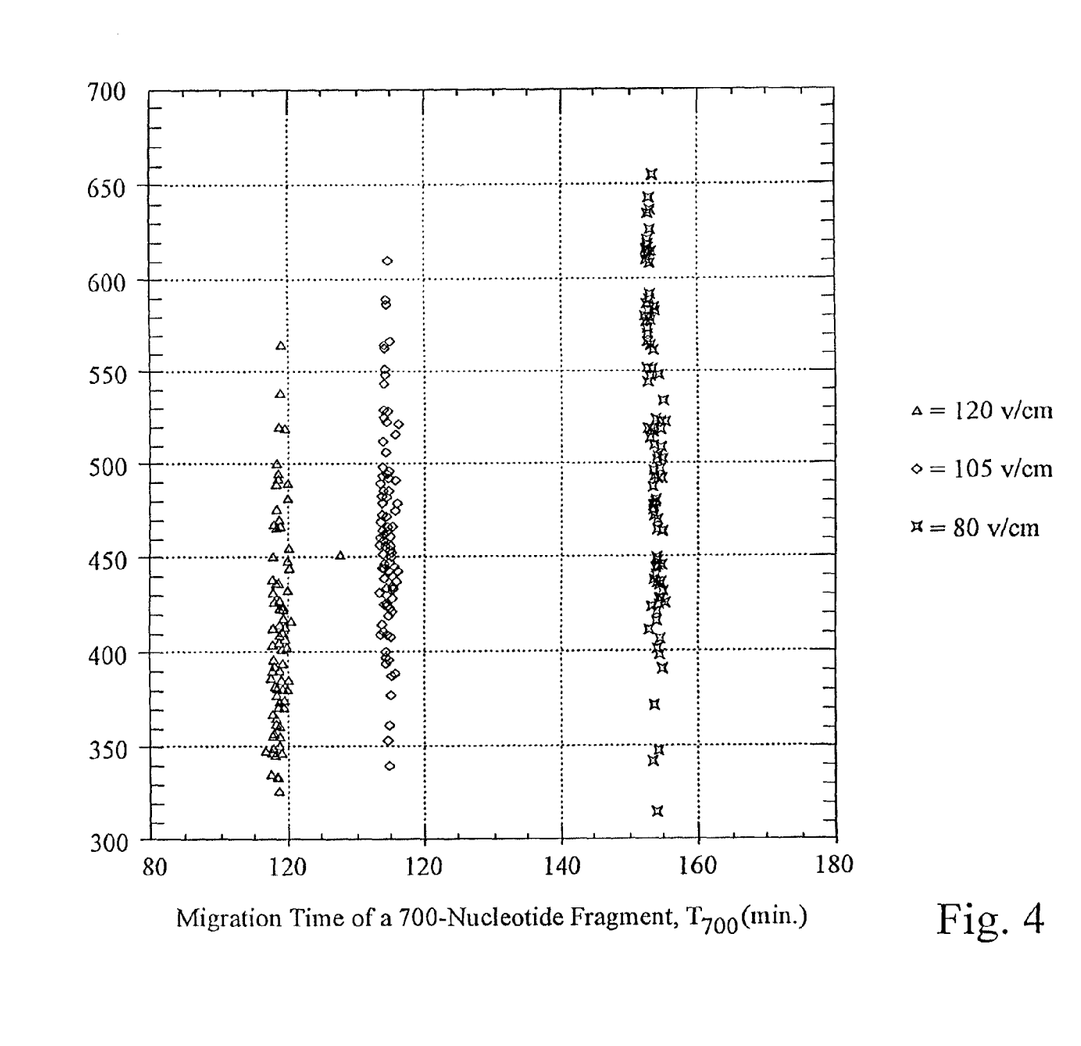
FIG. 4 shows a plot of LOR vs. migration time of a 700-nucleotide DNA fragment in approximately 96 different capillaries at each of a number of run fields without the use of an initial electric field ramp and using a separation medium containing 6M urea.

FIGS. 3 and 4 show, at each of a number of different run fields, the LOR value for each of about 96 different electropherograms. In FIG. 3 the separation medium contained 8 M urea denaturant while in FIG. 4 the separation medium contained 6 M urea. The y-axis of each plot indicates the LOR value, while the x-axis of each plot indicates the time required for a 700 nucleotide fragment to reach the detector, $T_{700}$. As can be clearly seen from the data, for both separation media, as the electric field is increased, and thus $T_{700}$ decreased, the average value of the LOR, $LOR_{avg}$, decreased, and the standard deviation of the LOR, $SD_{LOR}$, increased. In addition, the magnitude of $SD_{LOR}$ was large in comparison with $LOR_{avg}$. Values for $LOR_{avg}$ and $SD_{LOR}$ for the data of FIGS. 3 and 4 are presented in Tables 2 and 3 immediately below. Thus, these data indicate that when the speed of the analysis is increased by increasing the run field, a substantial penalty of reduced LOR and increased $SD_{LOR}$ is paid. For example, according to the data presented in Table 2 below, by increasing the run field from 90 V/cm to 130 V/cm, a reduction in LOR of 165 nuleotides was observed.

TABLE 2

FIG. 3 Data (8 M Urea)

| E (V/cm) | $LOR_{avg}$ | $SD_{LOR}$ |
|---|---|---|
| 90 | 632 | 29 |
| 105 | 583 | 48 |
| 120 | 528 | 58 |
| 130 | 467 | 69 |

TABLE 3

FIG. 4 Data (6 M Urea)

| E (V/cm) | $LOR_{avg}$ | $SD_{LOR}$ |
|---|---|---|
| 80 | 501 | 93 |
| 105 | 461 | 53 |
| 120 | 407 | 93 |

Example 2

Effect of An Initial Electric Field Ramp on LOR as a Function of Run Field

Figure 5:
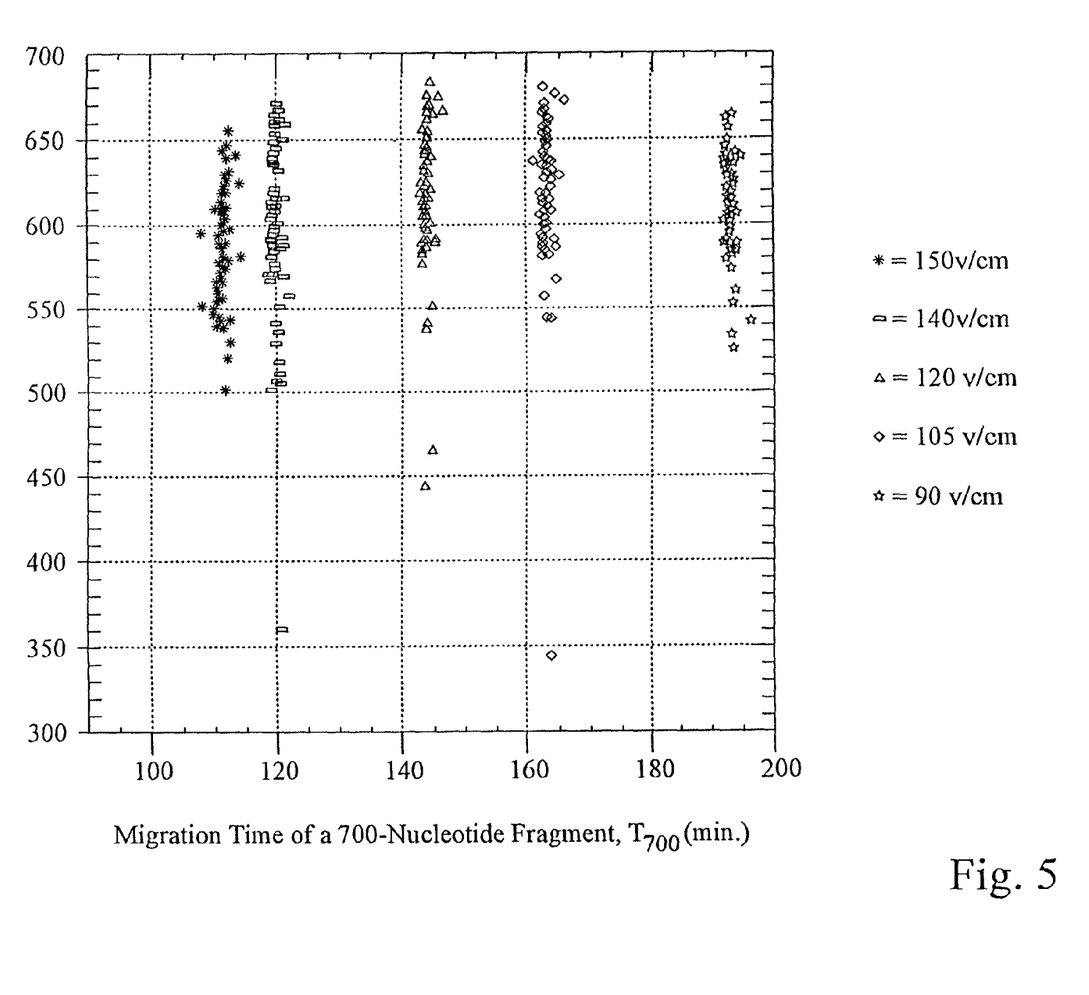
FIG. 5 shows a plot of LOR vs. migration time of a 700-nucleotide DNA fragment in approximately 96 different capillaries at each of a number of run fields with the use of an initial field ramp of 0.25 V/cm-s and using a separation medium containing 8M urea.
Figure 6:
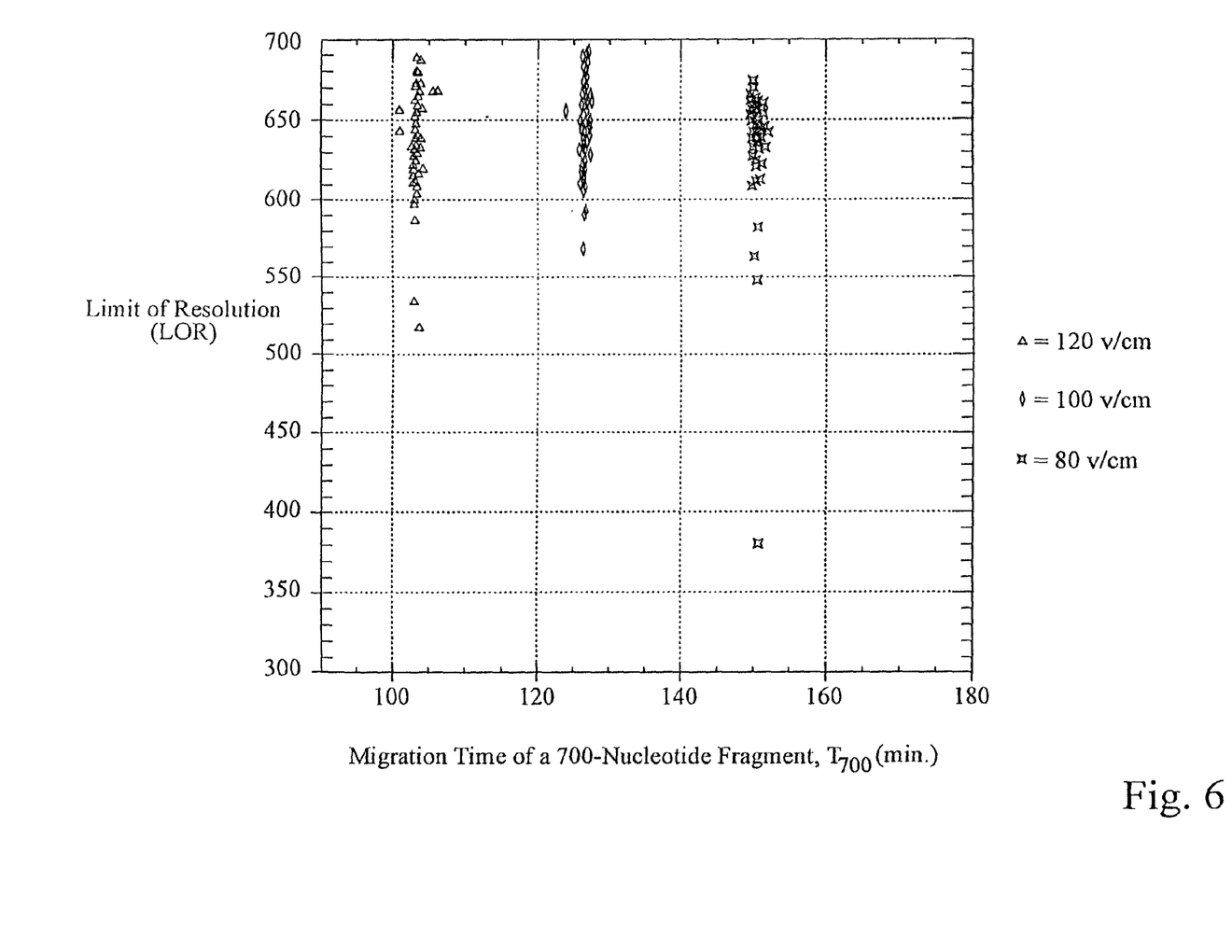
FIG. 6 shows a plot of LOR vs. migration time of a 700-nucleotide DNA fragment in approximately 96 different capillaries at each of a number of run fields with the use of an initial field ramp of 0.25 V/cm-s and using a separation medium containing 6M urea.

FIGS. 5 and 6, when compared with FIGS. 3 and 4, show the effect of a controlled initial electric field ramp on the LOR as a function of run field in two different separation media. In FIG. 5 the separation medium contained 8 M urea denaturant while in FIG. 6 the separation medium contained 6 M urea. In both the experiments of FIG. 5 and FIG. 6, the initial electric field ramp was 0.25 V/cm-s using a discontinuous step electric field vs. time profile where $\Delta E$ was 10 V/cm and $\Delta t$ was 40 s at each step. As can be clearly from the data, the introduction of the initial electric field ramp resulted in a substantial increase in $LOR_{avg}$ and decrease in $SD_{LOR}$ at each of the run fields studied. However, the effect was most pronounced for the higher electric fields. Thus, these data indicate that by using a controlled initial electric field ramp according to the present invention, higher run fields can be used without sacrificing separation performance, and consequently considerably shorter analysis times may be achieved, leading to significantly higher overall throughput. Values for $LOR_{avg}$ and $SD_{LOR}$ for the data of FIGS. 5 and 6 are presented in Tables 4 and 5 immediately below.

TABLE 4

FIG. 5 Data (8 M Urea)

| E (V/cm) | $LOR_{avg}$ | $SD_{LOR}$ |
|---|---|---|
| 90 | 611 | 29 |
| 105 | 621 | 41 |
| 120 | 619 | 40 |
| 140 | 608 | 49 |
| 150 | 589 | 32 |

TABLE 5

FIG. 6 Data (6 M Urea)

| E (V/cm) | $LOR_{avg}$ | $SD_{LOR}$ |
|---|---|---|
| 80 | 643 | 33 |
| 100 | 645 | 24 |
| 120 | 643 | 33 |

Example 3

Effect of Ramp Rate on LOR

Figure 7:
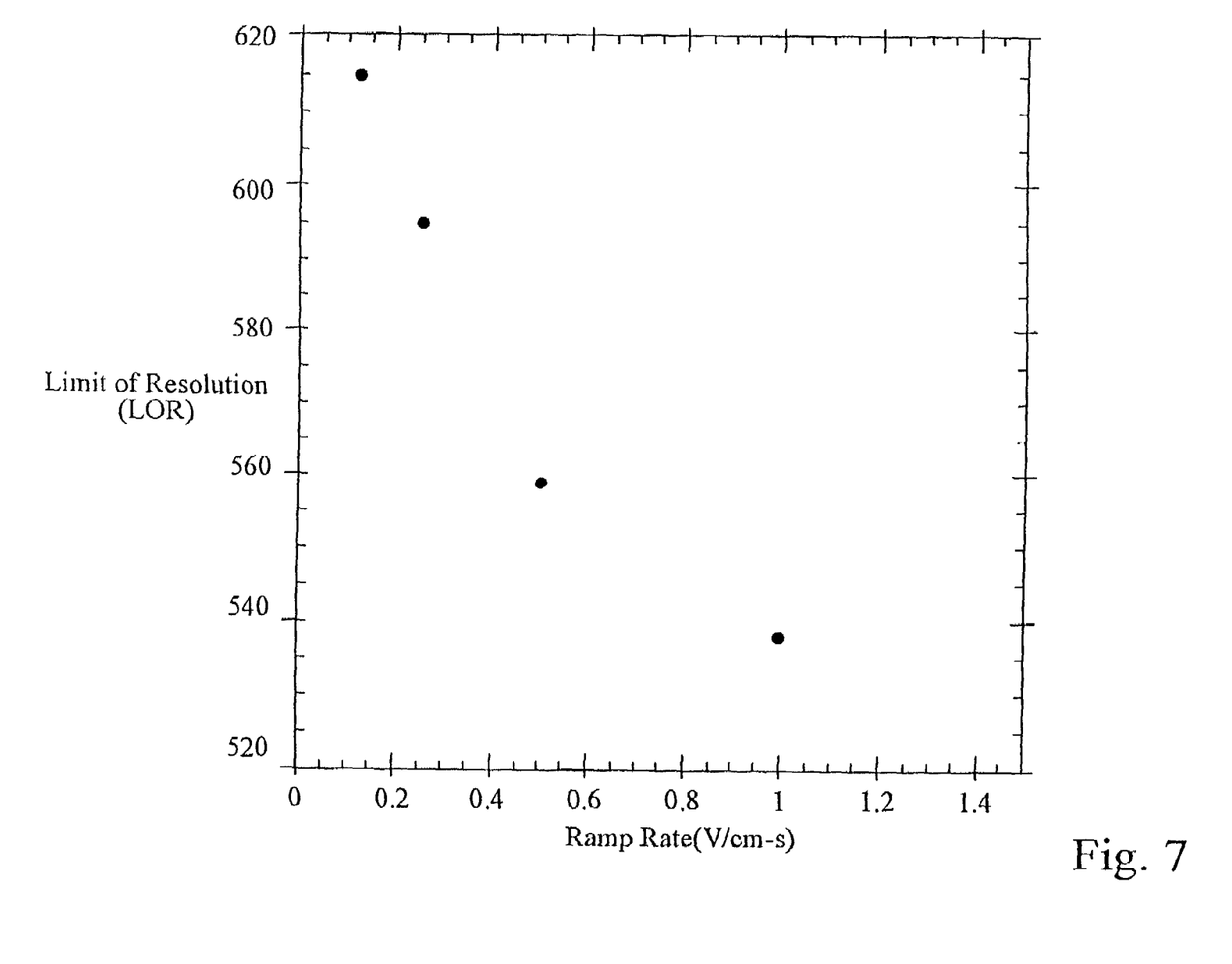
FIG. 7 shows the effect of various ramp rates of an initial electric field ramp on LOR using a run field of 160 V/cm and a separation medium containing 8M urea.
Figure 8:
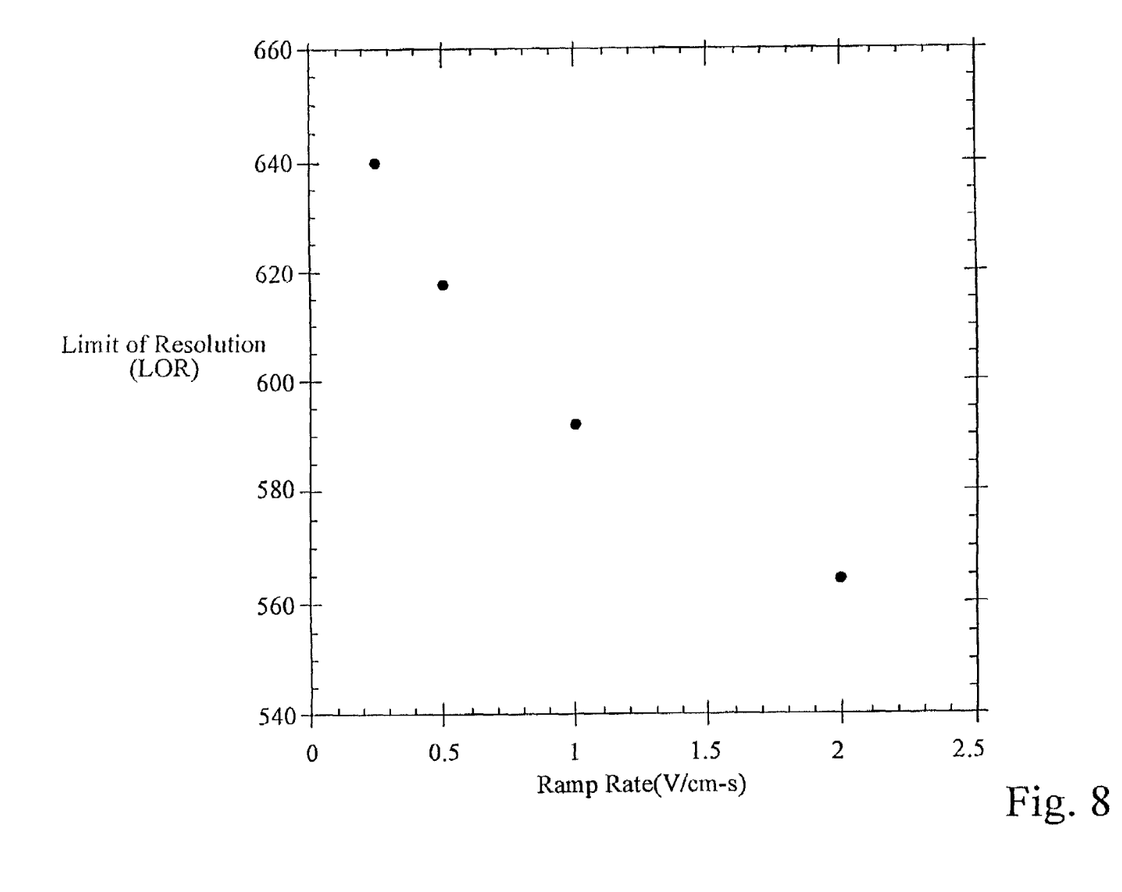
FIG. 8 shows the effect of various ramp rates of an initial electric field ramp on the limit of resolution using a run field of 120 V/cm and a separation medium containing 6M urea.

FIGS. 7 and 8 show the effect of the ramp rate of the initial electric field ramp on LOR at two different run fields in two different separation media. Each of the initial electric field ramps comprised a discontinuous step electric field vs. time profile in which for each ramp rate the values of $\Delta E$ and $\Delta t$ were equal.

In FIG. 7 the run field was 160 V/cm and the separation medium contained 8 M urea. The different ramp rates shown in FIG. 7 were achieved by holding $\Delta E$ at 500 V and varying $\Delta t$ between 10 and 80 seconds. As can be clearly seen by the data in FIG. 7, using a ramp rate of about 0.12 V/cm-s resulted in an increase of LOR of almost 80 nucleotides.

In FIG. 8 the run field was 120 V/cm and the separation medium contained 6 M urea. The different ramp rates were achieved by holding $\Delta E$ at 500 V and varying $\Delta t$ between 5 and 40 seconds. As can be clearly seen by the plot in FIG. 8, using a ramp rate of about 0.25 V/cm-s resulted in an increase of LOR of almost 100 nucleotides.

Example 4

Figure 9:
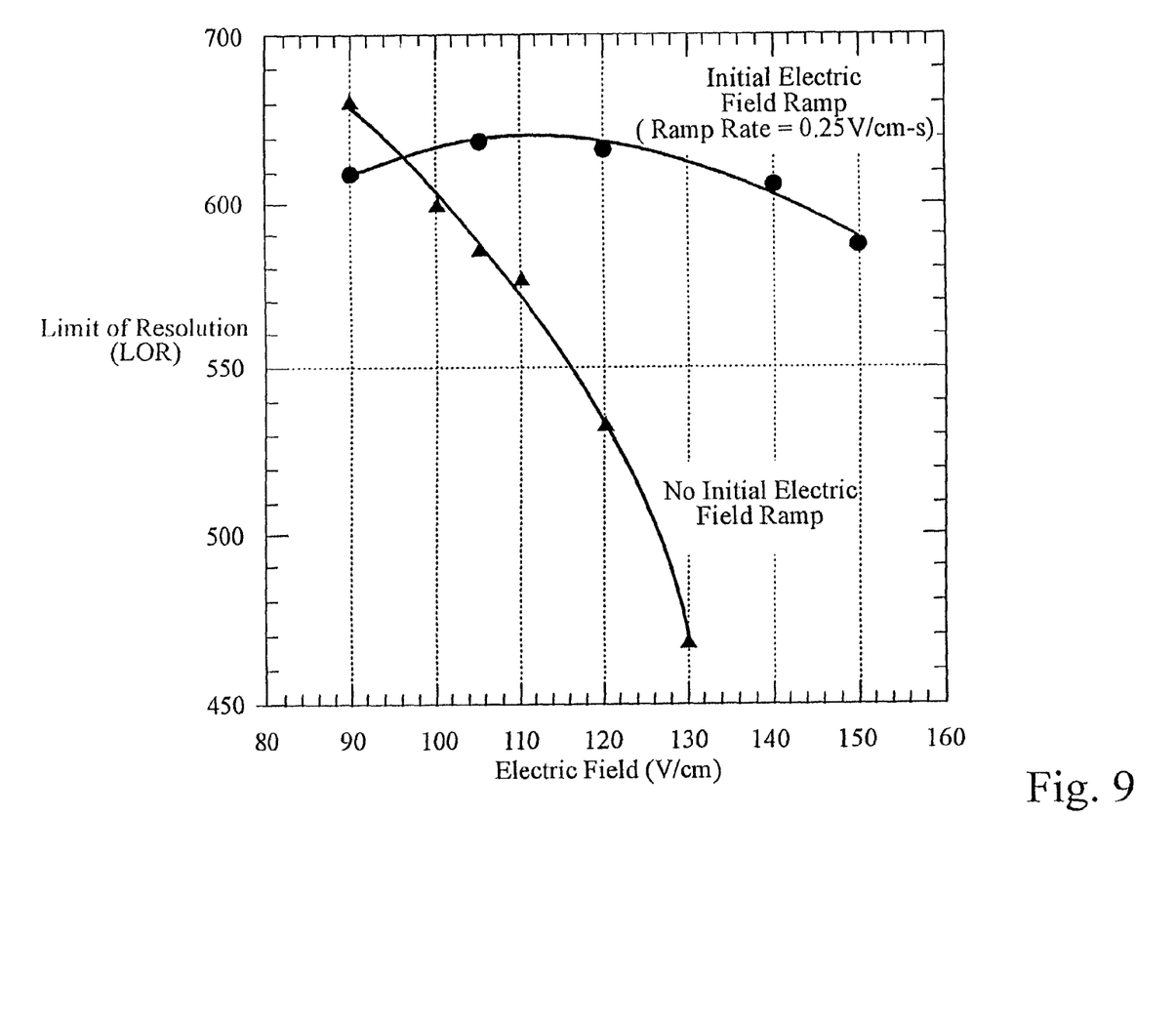
FIG. 9 shows the effect of using an initial electric field ramp having a ramp rate of 0.25 V/cm-s on LOR as a function of run field in a separation medium containing 8M urea.
Figure 10:
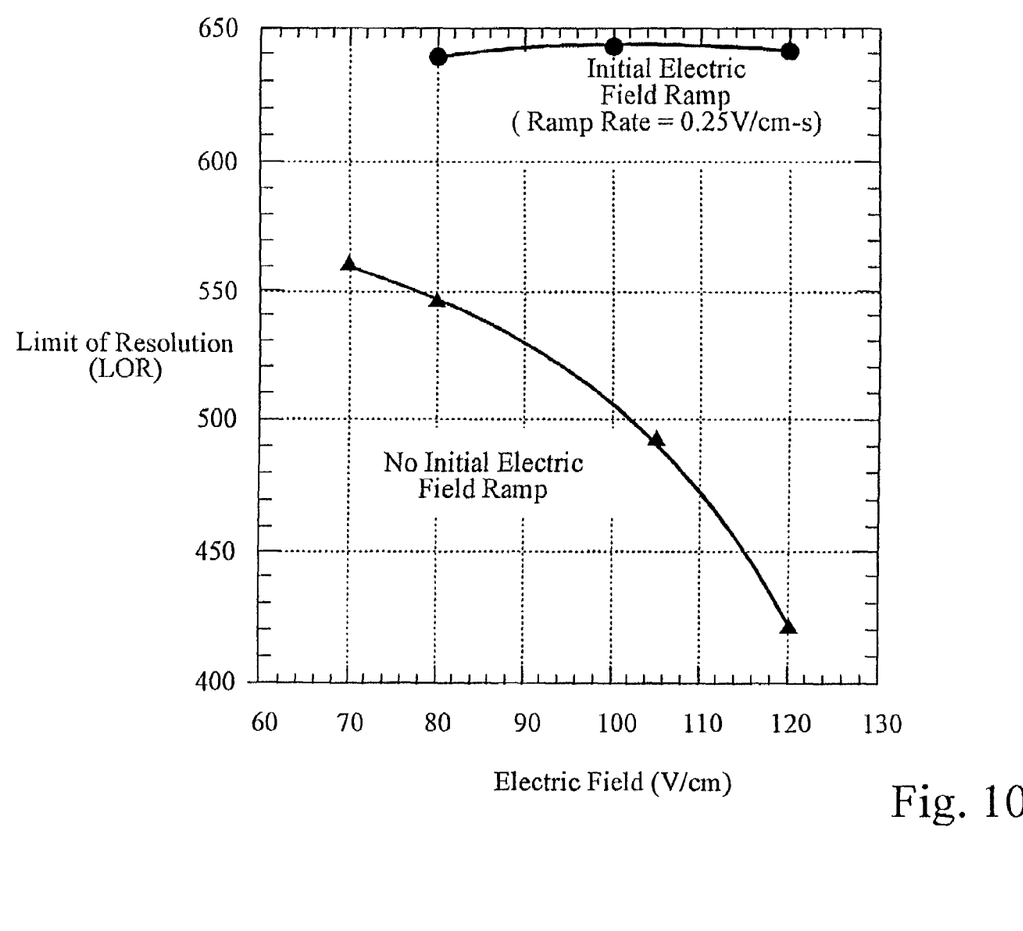
FIG. 10 shows the effect of using an initial electric field ramp having a ramp rate of 0.25 V/cm-s on LOR as a function of run field in a separation medium containing 6M urea.

Effect of Using an Initial Electric Field Ramp on LOR as a Function of Run Field FIGS. 9 and 10 demonstrate the effect of using an initial electric field ramp on LOR as a function of run field. The ramp rate of the initial electric field ramp was 0.25 V/cm-s in both cases where the initial electric field ramps were achieved using a discontinuous step electric field vs. time profile in which the value of $\Delta E$ was 10 V/cm and the value of $\Delta t$ was 40 s. In FIG. 9, the separation medium contained 8M urea and in FIG. 10 the separation medium contained 6M urea. The plots shown in both FIGS. 9 and 10 clearly illustrate the dramatic effect that an initial electric field ramp can have on separation performance, and also indicate that this effect becomes more pronounced at higher run fields. The dramatic effect of using an initial electric field ramp on the speed of a separation can also bee clearly seen in the data of FIGS. 9 and 10. For example, referring to FIG. 10, to achieve a LOR of 600 without the use of an initial electric field ramp, the run field cannot exceed 100 V/cm, while, if an initial electric field ramp of 0.25 V/cm-s is employed, a run field of 150 V/cm may be used, resulting in a decrease in analysis time of approximately 50% (not including the ten minutes required to effect the initial electric field ramp).

All publications and patent applications are herein incorporated by reference to the same extent as if each individual publication or patent application was specifically and individually indicated to be incorporated by reference.

Although only a few embodiments have been described in detail above, those having ordinary skill in the electrophoresis art will clearly understand that many modifications are possible in the preferred embodiment without departing from the teachings thereof. For example, one may practice the present invention using both controlled initial electric field ramp and temperature ramp protocols in combination. All such modifications are intended to be encompassed within the following claims.

We claim:

1. In a capillary electrophoresis method in which analyte species are separated by differential electrophoretic migration through a fluid separation medium under the influence of a constant run field, an improvement for reducing peak broadening caused when the constant run field is established comprising:
    establishing the constant run field at a ramp rate no greater than about 5 V/cm-s;
    wherein the fluid separation medium is a buffered solution containing a non-crosslinked polymer and the analyte species are nucleic acid.

2. The method of claim 1, wherein the run field ranges from about 50 V/cm to about 3,000 V/cm.

3. The method of claim 1, wherein the run field ranges between about 80 V/cm and 500 V/cm.

4. The method of claim 1, wherein the run field is established over a period of at least about 10 seconds.

5. The method of claim 1, wherein the run field is established over a period ranging from about 20 seconds to about 4,000 seconds.

6. The method of claim 1, wherein the ramp rate ranges from about 0.1 V/cm-s to about 1.0 V/cm-s.

7. The method of claim 1, wherein peak broadening associated with establishment of a run field is reduced at least about 10% compared to that found when the run field is established not using a ramp rate.

8. The method of claim 7, wherein peak broadening is reduced at least about 25%.

9. The method of claim 8, wherein peak broadening is reduced at least about 40%.

10. In a capillary electrophoresis method in which analyte species are separated by differential electrophoretic migration through a fluid separation medium under the influence of a constant run field, an improvement for reducing peak broadening caused when the constant run field is established comprising:
    establishing the constant run field at a ramp rate no greater than about 5 V/cm-s;
    wherein the analyte species are nucleic acid.

11. The method of claim 10, wherein the run field ranges from about 50 V/cm to about 3,000 V/cm.

12. The method of claim 10, wherein the run field ranges between about 80 V/cm and 500 V/cm.

13. The method of claim 10, wherein the run field is established over a period of at least about 10 seconds.

14. The method of claim 10, wherein the run field is established over a period ranging from about 20 seconds to about 4,000 seconds.

15. The method of claim 10, wherein the ramp rate ranges from about 04 V/cm-s to about 1.0 V/cm-s.

16. The method of claim 10, wherein peak broadening associated with establishment of a run field is reduced at least about 10% compared to that found when the run field is established not using a ramp rate.

17. The method of claim 16, wherein peak broadening is reduced at least about 25%.

18. The method of claim 17, wherein peak broadening is reduced at least about 40%.

* * * * *